(12) United States Patent  
Kakiuchi et al.

(10) Patent No.: US 8,517,983 B2  
(45) Date of Patent: Aug. 27, 2013

(54) DUAL CHAMBER COMBINED CONTAINER-SYRINGE

(75) Inventors: Makoto Kakiuchi, Ibaraki-ken (JP); Seiji Shimazaki, Ibaraki-ken (JP); Teruo Matsuda, Ibaraki-ken (JP)

(73) Assignee: Arte Corporation, Tokyo (JP)

( * ) Notice: Subject to any disclaimer, the term of this patent is extended or adjusted under 35 U.S.C. 154(b) by 0 days.

(21) Appl. No.: 13/276,273

(22) Filed: Oct. 18, 2011

(65) Prior Publication Data

US 2012/0095394 A1    Apr. 19, 2012

(30) Foreign Application Priority Data

Oct. 19, 2010    (JP) .................................. 2010-234873

(51) Int. Cl.  
*A61M 37/00*    (2006.01)

(52) U.S. Cl.  
USPC .................................. 604/89; 604/90; 604/92

(58) Field of Classification Search  
USPC ............................................. 604/82–92, 187  
See application file for complete search history.

(56) References Cited

U.S. PATENT DOCUMENTS 5,080,649 A * 1/1992 Vetter ............................... 604/91  
7,311,692 B2 * 12/2007 Kato et al. ....................... 604/91

FOREIGN PATENT DOCUMENTS

| CN | 1750852 A | 3/2006 |
| JP | 04-033233 | 6/1992 |
| JP | 07-039582 | 2/1995 |
| JP | 2514472 | 7/1996 |
| JP | 2642582 | 8/1997 |
| JP | 3301768 | 7/2002 |
| JP | 2007-111156 | 5/2007 |
| JP | 2008-104623 | 5/2008 |
| JP | 4417614 | 2/2010 |
| WO | 94/01150 A1 | 1/1994 |
| WO | 03/015854 A1 | 2/2003 |

OTHER PUBLICATIONS

Office Action issued by Japanese Patent Office in JP-2010-234873, dated Dec. 7, 2010.  
Chinese Office Action in Chinese Application No. 201110315200.2, mailed on Mar. 27, 2013.

* cited by examiner

*Primary Examiner* — Theodore Stigell  
(74) *Attorney, Agent, or Firm* — Nixon Peabody LLP

(57) ABSTRACT

A dual chamber combined container-syringe includes: an outer casing having a bypass portion; a hub lure lock; a front stopper; a middle stopper that seals a pharmaceutical preparation together with the front stopper; an end stopper that seals a liquid medicine together with the middle stopper; a finger grip; and a plunger rod that is connected to the end stopper from the rear end side, wherein a female screw portion twisted around an axis is formed on an inner peripheral surface of the finger grip, and a first male screw portion, a tip of which comes into contact with a rear end of the female screw portion and can be screwed into the female portion, and a first guide plate are formed on an outer peripheral surface of the plunger rod when a part of the middle stopper enters the bypass portion.

7 Claims, 10 Drawing Sheets

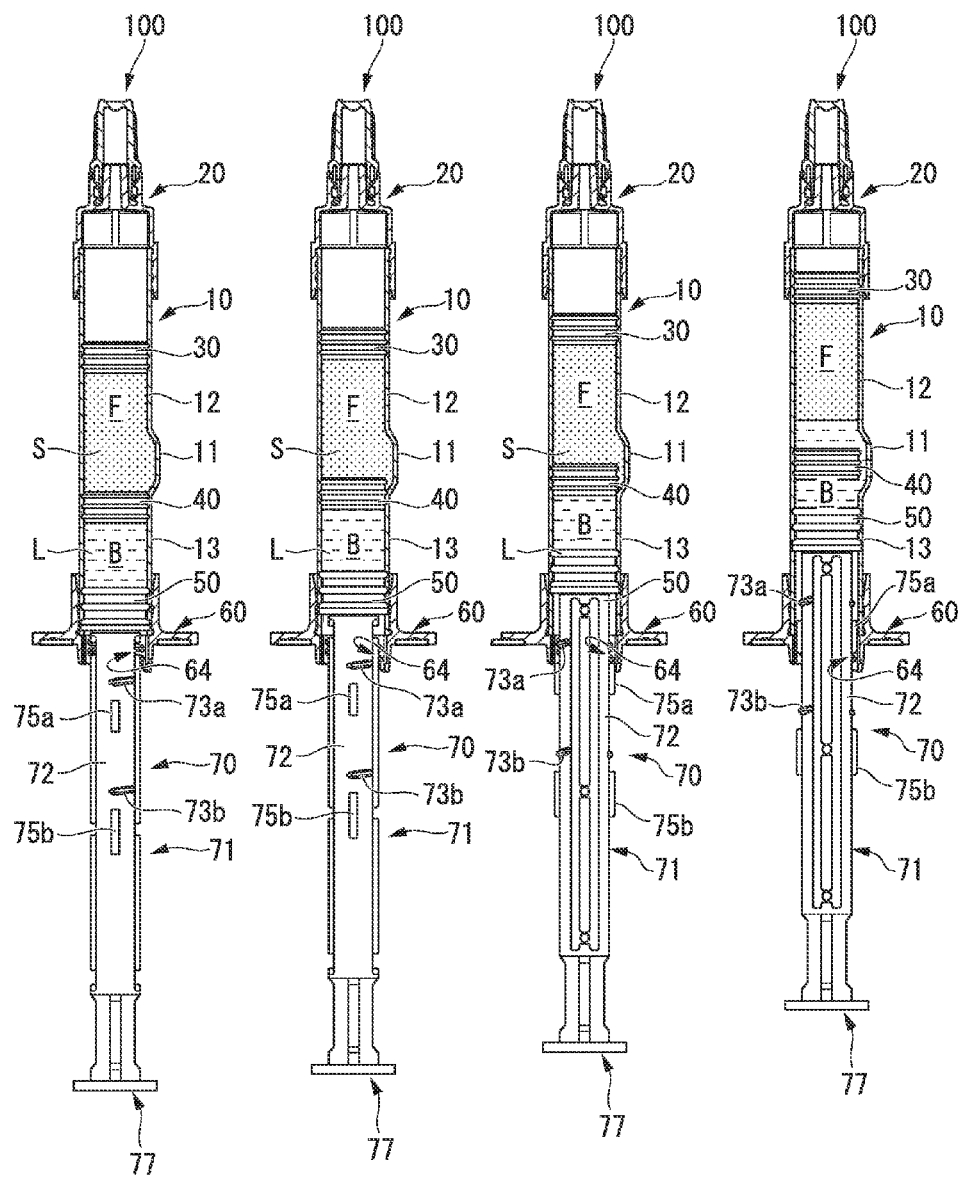

DUAL CHAMBER COMBINED CONTAINER-SYRINGE

BACKGROUND OF THE INVENTION

1. Field of the Invention

The present invention relates to a combined container-syringe that is filled with and contains a liquid medicine in advance and is capable of taking out from a packaging and immediately using the same when used.

Priority is claimed on Japanese Patent Application No. 2010-234873, filed Oct. 19, 2010, the content of which is incorporated herein by reference.

2. Description of Related Art

Since the combined container-syringe is filled with a liquid medicine in advance, the combined container-syringe can immediately be taken out from the packaging and used in a medical institution without a complicated operation. Since the combined container-syringe is extremely convenient and greatly contributes to the reduction of the work of those engaged in a medicine practice such as doctors or nurses, the combined container-syringe is adopted in many hospitals.

In the related art, as a kind of combined container-syringe, a dual chamber combined container-syringe is known in which a pharmaceutical preparation and a liquid medicine are separately filled.

The dual chamber combined container-syringe is configured such that a front stopper is fitted into a tip side of an outer casing, an end stopper is fitted into a rear end side thereof, and an inner portion of the outer casing is divided into two front and rear chambers by a middle stopper fitted into a central portion in the outer casing. Furthermore, in a portion of the tip side further forward than the middle stopper in the outer casing, a bypass portion is formed in which a part of an inner peripheral surface of the outer casing is formed so as to bulge outward. In addition, the front chamber of the tip side of the middle stopper is filled with powdered pharmaceutical preparation, and the tip thereof is sealed with the front stopper. Meanwhile, the rear chamber of the rear end side of the middle stopper is filled with the liquid medicine, and the rear end thereof is sealed with the end stopper. In addition, a plunger rod is connected to the rear end of the end stopper.

When using the dual chamber combined container-syringe having such a configuration, the end stopper is moved forward in the outer casing by pushing the plunger rod into the outer casing. Then, the pressing force due to the forward movement of the end stopper is transmitted to the middle stopper via the liquid medicine, whereby the middle stopper is moved forward along with the forward movement of the end stopper. Moreover, when the middle stopper reaches the bypass portion, the two front and rear chambers of the middle stopper communicate with each other via the bulged portion of the bypass portion. As a result, the liquid medicine of the rear chamber flows in the front chamber, and the liquid medicine and the pharmaceutical preparation of the front chamber are mixed with each other, whereby an injection drug is prepared.

Japanese Unexamined Patent Application, First Publication No. 2007-111156 is an example of the above-described related art.

In the dual chamber combined container-syringe mentioned above, in order that the liquid medicine and the pharmaceutical preparation can be suitably mixed with each other, until the entire liquid medicine of the rear chamber flows in the front chamber, the middle stopper needs to remain in the bypass portion. Furthermore, in the case of a pharmaceutical preparation that is not easily dissolved, there is a need to control the inflow of the liquid medicine.

However, when the plunger rod is pressed too fast, or when the plunger rod is too strongly pushed without confirming the ending of the inflow of the liquid medicine to the front chamber, the middle stopper is moved to the tip side further than the bypass portion in the state in which not all the liquid medicine can flow in the front chamber. As a result, a situation is generated where the liquid medicine in the rear chamber remains without being mixed with the pharmaceutical preparation.

In this manner, depending on an erroneous operation of the plunger rod, an unnecessary liquid medicine is generated which is never mixed with the pharmaceutical preparation. As a consequence, there is a problem in that the injection drug of a given concentration cannot be prepared, and the pharmaceutical preparation is not sufficiently dissolved by the liquid medicine.

The present invention was made in view of the problems, and an object thereof is to provide a dual chamber combined container-syringe that is capable of reliably and suitably mixing the liquid medicine with the pharmaceutical preparation according to the natures thereof.

SUMMARY OF THE INVENTION

In order to solve the problem, the present invention suggests apparatuses as below.

That is, a dual chamber combined container-syringe according to an aspect of the present invention includes an outer casing which forms a cylinder shape around an axis and has a bypass portion formed by an outward bulging of a part of an inner peripheral surface; a hub lure lock provided in a tip of the outer casing; a finger grip provided in a rear end of the outer casing; a front stopper that is fitted to a tip side of the bypass portion in the outer casing; a middle stopper that is fitted to a rear end side of the bypass portion in the outer casing and seals the pharmaceutical preparation together with the front stopper; and an end stopper that is fitted to a rear end side of the middle stopper in the outer casing and seals the liquid medicine together with the middle stopper; and a plunger rod that is inserted into the finger grip and is connected to the end stopper from the rear end side, wherein an inner peripheral surface of the finger grip is formed with a female screw portion twisted around the axis, and an outer peripheral surface of the plunger rod is formed with a first male screw portion that is capable of being screwed into the female screw portion, whereby when a part of the middle stopper, which is moved forward, enters the bypass portion by pushing the plunger rod, a tip of the first male screw portion can come into contact with and can be screwed into a rear end of the female screw portion, and before the entire middle stopper, which is moved forward, enters the bypass portion by rotating the plunger rod according to the first male screw portion and the female screw portion being screwed, the first male screw portion and the female screw portion are unscrewed.

According to the dual chamber combined container-syringe having such a characteristic, when the middle stopper is moved forward via the end stopper and the liquid medicine by pushing the plunger rod, the tip of the first male screw portion comes into contact with the rear end of the female screw portion when a part of the middle stopper portion enters the bypass portion. Moreover, next, if not rotating the plunger rod according to the screwing of the first male screw portion and the female screw portion, the plunger rod cannot be moved forward. Thus, even when further pushing the plunger rod, the plunger rod is not moved forward, and the middle stopper is not moved forward. Thus, it is possible to avoid a case where the middle stopper mistakes the timing entering the bypass portion and is moved forward up to the tip side of the bypass portion too much.

Furthermore, when the middle stopper is moved forward by rotating the plunger rod according to the first male screw portion and the female screw portion being screwed, before the entire middle stopper enters the bypass portion, the first male screw portion and the female screw portion are unscrewed, whereby the pushing of the plunger rod is possible.

In addition, when a part of the middle stopper enters the bypass portion refers to when a part of the middle stopper enters the bypass portion, or immediately before the tip of the middle stopper reaches the rear end of the bypass portion, other than when the tip of the middle stopper reaches the rear end of the bypass portion. That is, a configuration may be adopted in which, before and after the tip of the middle stopper reaches the bypass portion, the tip of the first male screw portion reaches the rear end of the female screw portion.

Furthermore, the dual chamber combined container-syringe according to the aspect of the present invention preferably includes a guide groove that is formed in the female screw portion and is extended parallel to the axis, and a first guide plate that is formed on the rear end side of the first male screw portion on the outer peripheral surface of the plunger rod and is guided along the guide groove.

After the first male screw portion passes through the female screw portion by rotating the plunger rod, the first male screw portion and the female screw portion are unscrewed, whereby the plunger rod enters a state in which it is capable of moving straight forward. At this time, by fitting the first guide plate of the plunger rod into the guide groove formed in the female screw portion, the plunger rod can be guided along the extension direction of the guide groove when pushing the plunger rod. As a result, it is possible to cause the plunger rod to move straight forward, in the manner of a general syringe.

In addition, the dual chamber combined container-syringe according to the aspect of the present invention preferably includes a first protrusion that is formed in the rear end of the finger grip and with which the first guide plate comes into contact so that the first guide plate can move thereover when the first male screw portion is screwed into the female screw portion, and after the first guide plate moves over the first protrusion, the female screw portion and the first male screw portion are unscrewed.

As a result, when rotating the plunger rod after the first male screw portion comes into contact with the female screw portion, a health care professional can perceive that the first male screw portion is screwed into the female screw portion.

Furthermore, when a part of the middle stopper enters the bypass portion, it is possible to enable a health care professional to easily and reliably perceive that state and focus their attention so as to carefully perform the next process.

Furthermore, the dual chamber combined container-syringe according to the aspect of the present invention preferably further includes a second protrusion that is formed in the rear end of the finger grip and with which the first guide plate moving over the first protrusion comes into contact in a position capable of being fitted into the guide groove.

As a result, when the first guide plate comes into contact with the second protrusion by rotating the plunger rod, it is possible to fit the first guide plate of the plunger rod into the guide groove of the finger grip. Thus, after that, by pushing the plunger rod, it is possible move the plunger rod forward in a straight manner.

In addition, in the dual chamber combined container-syringe according to the aspect of the present invention, it is desirable that a second male screw portion capable of being screwed into the female screw portion is formed in the rear end side of the first guide plate on the outer peripheral surface of the plunger rod, and after a part of the middle stopper, which is moved forward, moves over the bypass portion by pushing the plunger rod, the tip of the second male screw portion can come into contact with and can be screwed into the rear end of the female screw portion, and, before a rear portion of the end stopper, which is moved forward, passes through the bypass portion by rotating the plunger rod according to the second male screw portion and the female screw portion being screwed, the second male screw portion and the female screw portion are unscrewed.

After the first male screw portion passes through the female screw portion, by the plunger rod being pushed in a straight manner, the plunger rod is moved forward. The liquid medicine of a rear chamber pressed by the end stopper by moving the plunger rod forward is moved to a front chamber via the bypass portion. At that time, the middle stopper is not moved from the bypass portion. Thus, the tip of the end stopper, which has been moved straight forward, comes into contact with the rear end of the middle stopper. In addition, when the middle stopper and the end stopper are moved forward in the contacting state by pushing the plunger rod, before the rear portion of the end stopper passes through the bypass portion, the tip of the second male screw portion comes into contact with the rear end of the female screw portion. As a result, a health care professional can easily recognize that a space between the middle stopper and the front stopper, that is a space where the liquid medicine is mixed with the pharmaceutical preparation, is sealed again. Thus, by shaking the dual chamber combined container-syringe at this time, it is possible to prepare an injection drug in which the pharmaceutical preparation is completely dissolved in the liquid medicine.

Furthermore, the dual chamber combined container-syringe according to the aspect of the present invention further includes a second guide plate that is formed at the rear end side of the second male screw portion on the outer peripheral surface of the plunger rod and is guided along the guide groove.

When rotating and moving forward the plunger rod according to the second male screw portion and the female screw portion being screwed, the second male screw portion passes through the female screw portion, whereby the second male screw portion and the female screw portion are unscrewed. As a result, the plunger rod enters a pushable state.

At this time, for example, by stopping the second guide plate of the plunger rod and the guide groove formed in the female screw portion in a fittable position and pushing the plunger rod, the plunger rod can be guided along the extension direction of the guide groove. As a result, it is possible to reliably switch the plunger rod from the rotation to the straight forward movement. Thus, by causing the plunger rod to go straight, it is possible to reliably perform the elimination of air bubbles in the outer casing and an administration of the liquid medicine to a patient.

In addition, in the dual chamber combined container-syringe according to the aspect of the present invention, it is desirable that the first protrusion comes into contact with the second guide plate so that the second guide plate can climb thereover when the second male screw portion is screwed into the female screw portion, and after the second guide plate climbs over the first protrusion, the second male screw portion and the female screw portion are unscrewed.

As a result, when rotating the plunger rod after the second male screw portion comes into contact with the female screw portion, a health care professional can perceive that the second male screw portion is screwed into the female screw portion.

In addition, in the dual chamber combined container-syringe according to the aspect of the present invention, it is desirable that the second protrusion comes into contact with the second guide plate in a position where the second guide plate climbing over the first protrusion can be fitted into the guide groove.

As a result, by rotating the plunger rod, when the second guide plate comes into contact with the second protrusion, the second guide of the plunger rod can be fitted into the guide groove of the finger grip. Thus, after that, by pushing the plunger rod, it is possible to move the plunger rod forward in a straight manner.

Meanwhile, a dual chamber combined container-syringe according to another aspect of the present invention includes an outer casing which forms a cylinder shape around an axis and has a bypass portion formed by an outward bulging of a part of an inner peripheral surface; a hub lure lock provided in a tip of the outer casing; a finger grip provided in a rear end of the outer casing; a front stopper that is fitted to a tip side of the bypass portion in the outer casing; a middle stopper that is fitted to a rear end side of the bypass portion in the outer casing and seals the pharmaceutical preparation together with the front stopper; and an end stopper that is fitted to a rear end side of the middle stopper in the outer casing and seals the liquid medicine together with the middle stopper; and a plunger rod that is inserted into the finger grip and is connected to the end stopper from the rear end side, wherein an inner peripheral surface of the finger grip is formed with a female screw portion twisted around the axis, and a second male screw portion capable of being screwed into the female screw portion is formed on an outer peripheral surface of the plunger rod, whereby after a part of the middle stopper, which is moved forward, passes through the bypass portion by pushing the plunger rod, a tip of the second male screw portion can come into contact with and can be screwed into a rear end of the female screw portion, and before the rear portion of the end stopper, which is moved forward, passes through the bypass portion by rotating the plunger rod according to the second male screw portion and the female screw portion being screwed, the second male screw portion and the female screw portion are unscrewed.

In addition, the dual chamber combined container-syringe according to the aspect of the present invention preferably includes a guide groove that is formed in the female screw portion of the finger grip and is extended parallel to the axis, and a second guide plate that is formed on the rear end side of the second male screw portion on the outer peripheral surface of the plunger rod and is guided along the guide groove.

Furthermore, the dual chamber combined container-syringe according to the aspect of the present invention preferably includes a first protrusion that is formed in the rear end of the finger grip and with which the second guide plate comes into contact so that the second guide plate can move thereover when the second male screw portion is screwed into the female screw portion.

In addition, the dual chamber combined container-syringe according to the aspect of the present invention preferably further includes a second protrusion with which the first guide plate climbing over the first protrusion comes into contact in a position capable of being fitted into the guide groove.

Furthermore, in the dual chamber combined container-syringe according to the aspect of the present invention, it is desirable that the first male screw portion capable of being screwed into the female screw portion is formed at the tip side of the second male screw portion on the outer peripheral surface of the plunger rod, when a part of the middle stopper which is moved forward, enters the bypass portion by pushing the plunger rod, the tip of the first male screw portion can come into contact with and can be screwed into the rear end of the female screw portion, and before the entire middle stopper, which is moved forward, enters the bypass portion by rotating the plunger rod according to the second male screw portion and the female screw portion being screwed, the male screw portion and the female screw portion are unscrewed.

According to the dual chamber combined container-syringe of an aspect of the present invention, when pushing the plunger rod, the tip of the first male screw portion of the plunger rod comes into contact with the rear end of the female screw portion of the finger grip, whereby, even when further pushing the plunger rod, the plunger rod is not further moved forward. As a result, it is possible to avoid a case where the speed of pushing the plunger rod into the outer casing or pushing force is too high, the middle stopper cannot be stopped in the bypass portion and is moved forward up to the tip side of the bypass portion. Thus, it is possible to make the middle stopper easily remain in the bypass portion, whereby it is possible to suitably mix the liquid fluid with the pharmaceutical preparation.

BRIEF DESCRIPTION OF THE DRAWINGS

FIG. 6A is a diagram that shows a usage method of the dual chamber combined container-syringe according to an embodiment.

FIG. 6B is a diagram that shows a usage method of the dual chamber combined container-syringe according to an embodiment.

FIG. 6C is a diagram that shows a usage method of the dual chamber combined container-syringe according to an embodiment.

FIG. 6D is a diagram that shows a usage method of the dual chamber combined container-syringe according to an embodiment.

DETAILED DESCRIPTION OF THE INVENTION

Hereinafter, a dual chamber combined container-syringe according to the embodiment of the present invention will be described in detail with reference to the drawings.

Figure 1:
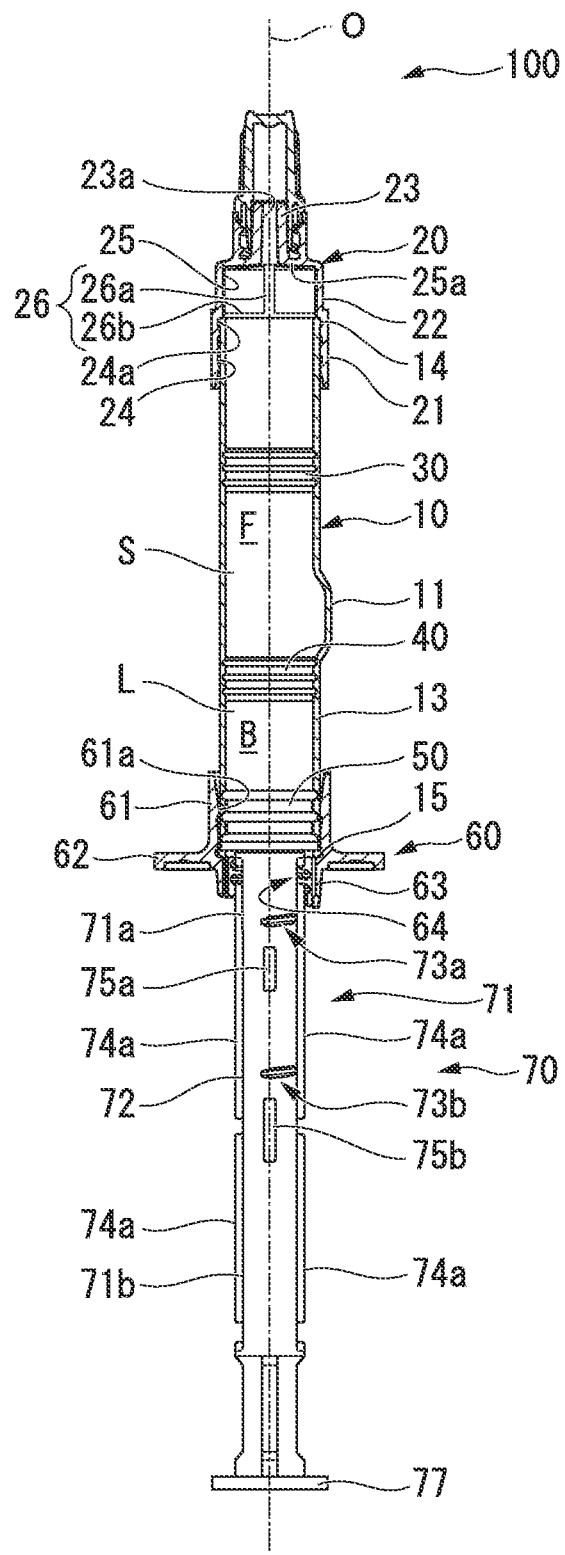
FIG. 1 is a longitudinal cross-sectional view of a dual chamber combined container-syringe according to an embodiment.
Figure 7A:
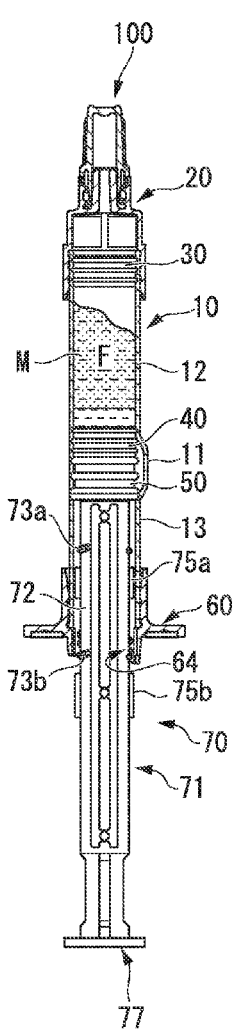
FIG. 7A is a diagram that shows a usage method of the dual chamber combined container-syringe according to an embodiment.

As shown in FIG. 1, a dual chamber combined container-syringe 100 includes an outer casing 10, a hub lure lock 20, a front stopper 30, a middle stopper 40, an end stopper 50, a finger grip 60, and a plunger rod 70. The dual chamber combined container-syringe 100 is filled with a pharmaceutical preparation S and a liquid medicine L, which prepare an injection drug M (see FIGS. 7A and 7B) by being mixed, in a separated state (see FIGS. 6A and 6B).

The outer casing 10 is molded from a transparent glass and is formed in an approximately cylindrical shape extended along an axis O. An approximately central portion of the outer casing 10 in the axial O direction is formed of a bypass portion 11 in which a part of an outer peripheral surface and an inner peripheral surface of the outer casing 10 in a circumferential direction bulges outward in a radial direction over a predetermined size of the axial O direction. In addition, a position of the bypass portion 11 in the axial O direction can be suitably set depending on the design.

Furthermore, a cylinder-shaped portion of the tip side of the bypass portion 11 in the outer casing 10 is a tip side cylinder portion 12, and a cylinder-shaped portion of the rear end side of the bypass portion 11 in the outer casing 10 is a rear end side cylinder portion 13. That is, in the outer casing 10, based on the boundary of the bypass portion 11, the tip side cylinder portion 12 is disposed at the tip side, and the rear end side cylinder portion 13 is disposed at the rear end side. In other words, in the outer casing 10, a region of the tip side is the tip side cylinder portion 12, a region of the rear end side is the rear end side cylinder portion 13, and a region between the region of the tip side and the region of the rear end side is the bypass portion 11.

Furthermore, at a tip outer periphery of the outer casing 10, a tip side ring-shaped protrusion 14 is formed which is protruded outward in the radial direction over the entire region of the circumferential direction. In addition, at a rear end outer periphery of the outer casing 10, a rear end side ring-shaped protrusion 15 is also formed which is protruded outward in the radial direction over the entire region in the circumferential direction.

The hub lure lock 20 is molded from a transparent synthetic resin having the suitable rigidity, and forms an exterior multistage cylindrical shape around the axis O. The hub lure lock 20 includes a proximal end portion 21 having a cylinder shape, a cylinder portion 22 that is joined to the tip side of the proximal end portion 21 such that the diameter is further reduced, and a lure point 23 that is formed at the further tip side of the cylinder portion 22 so as to have a diameter smaller than the cylinder portion 22.

A fitting hole 24, which is opened to the rear end side of the hub lure lock 20, is formed inside the proximal end portion 21, and a bypass chamber 25 of a hole shape with a bottom is formed in the front side of the fitting hole 24, that is, at the inside of the cylinder portion 22. A place corresponding to the bottom portion of the bypass chamber 25 is a front end surface 25a with which the tip of the front stopper 30 comes into contact. The front end surface 25a is formed in a conical surface shape that is gradually reduced in diameter as it goes toward the front side.

Furthermore, the inner portion of the lure point 23 is formed with an introduction hole 23a that is penetrated along the axis O. The introduction hole 23a is configured so that one end side thereof is opened to the tip of the lure point 23 and the other end side thereof is opened to the center of the front end surface 25a in the bypass chamber 25. An injection needle 27 (not shown in FIG. 1, see FIG. 7C) extending to the tip side along the axis O is attached to one end side of the introduction hole 23a, that is, the tip side, in a communicated state.

The fitting hole 24 is a hole that is formed for attaching the hub lure lock 20 to the outer casing 10, and the inner diameter thereof is formed so as to be approximately identical to the outer diameter of the outer casing 10. By fitting the fitting hole 24 onto the tip of the outer casing 10, the hub lure lock 20 is attached to the tip side of the outer casing 10.

Furthermore, the front end portion of the inner peripheral wall of the fitting hole 24 is formed with a ring-shaped groove 24a, which is recessed around the axis O in an annular shape. When attaching the hub lure lock 20 to the tip side of the outer casing 10, the front end side ring-shaped protrusion 14 of the outer casing 10 is fitted to the ring-shaped groove 24a, whereby the hub lure lock 20 is fixedly fixed to and integrated with the outer casing 10 in an air-tight and liquid-tight manner.

The bypass chamber 25 is a hole with a bottom that has an inner diameter smaller than the fitting hole 24, and an inner peripheral wall thereof is formed with a bypass groove 26. The bypass groove 26 includes a straight groove 26a and an annular groove 26b.

A plurality of straight grooves 26a is formed at equal distances in the circumferential direction so as to be extended parallel to the axis O on the inner wall surface of the bypass chamber 25. The tip sides of the straight grooves 26a are extended from the inner wall surface of the bypass chamber 25 to the front end surface 25a and are connected to the introduction hole 23a formed in the inner portion of the lure point 23, respectively.

Furthermore, the annular groove 26b is a ring-shaped groove that is extended around the axis O in the circumferential direction, and is formed in the vicinity of a boundary between the bypass chamber 25 and the fitting hole 24 on the inner wall surface of the bypass chamber 25. The annular grooves 26b are connected to the respective rear ends of the plurality of straight grooves 26a, whereby the respective straight grooves 26a are connected via the annular grooves 26b.

The front stopper 30, the middle stopper 40, and the end stopper 50 are molded from a medical rubber having a corrosion resistance to the pharmaceutical preparation S, the liquid medicine L, and the injection drug M, respectively, and are formed in an approximately cylindrical shape around the axis O having an outer diameter slightly larger than the inner diameter of the outer casing 10.

The front stopper 30 is inserted into the tip side of the bypass portion 11 in the outer casing 10, that is, the tip side cylinder portion 12.

Furthermore, the middle stopper 40 is inserted into the rear end side of the bypass portion 11 in the outer casing 10, that is, the rear end side cylinder portion 13. Particularly, the middle stopper 40 in the present embodiment is disposed such that the tip of the middle stopper 40 is situated in the boundary between the rear end side cylinder portion 13 becoming the tip of the rear end side cylinder portion 13 and the bypass portion 11. Moreover, a powdered pharmaceutical preparation S is sealed so as to be interposed between the front stopper 30 and the middle stopper 40 in the outer casing 10. That is, the pharmaceutical preparation S is filled in a front chamber F that is formed by the inner peripheral surface of the outer casing 10, the rear end surface of the front stopper 30, and the tip surface of the middle stopper 40.

The end stopper 50 is inserted into a further rear end side of the middle stopper 40 in the rear end side cylinder portion 13 of the outer casing 10 at a gap with the middle stopper 40 in the axial O direction. A liquid medicine L is sealed so as to be interposed between the end stopper 50 and the middle stopper 40. That is, the liquid medicine L is filled in a rear chamber B that is formed by the inner peripheral surface of the outer casing 10, the rear end surface of the middle stopper 40, and the tip surface of the end stopper 50. In addition, the rear end of the end stopper 50 is formed with a female screw hole (not shown) into which a connection portion 76 of a plunger rod 70 described later is screwed.

In this manner, in the dual chamber combined container-syringe 100, the pharmaceutical preparation S and the liquid medicine L are separately sealed in the front chamber F and the rear chamber B that are divided by the middle stopper 40.

As shown in FIG. 2, the finger grip 60 has a fitting portion 61, a flange portion 62, and a cylinder portion 63.

The fitting portion 61 has an approximately cylinder shape around the axis O, and the inner peripheral side thereof is a fitting hole 61a into which the rear end of the outer casing 10 is fitted. The rear end inner periphery of the fitting hole 61a is formed with a ring-shaped groove 61b that is recessed around the axis O in an annular shape. As shown in FIG. 1, when attaching the finger grip 60 to the rear end of the outer casing 10, the rear end side ring-shaped protrusion 15 of the outer casing 10 is fitted to the ring-shaped groove 61b, whereby the finger grip 60 is fixedly fixed to and integrated with the outer casing 10.

The flange portion 62 overhangs from the rear end of the fitting portion 61, that is, from the vicinity of the boundary between the fitting portion 61 and the cylinder portion 63 in a radial direction around the axis O, and forms an approximately rectangular shape when viewed from the axial O direction. The flange portion 62 has a role of facilitating the handling of the dual chamber combined container-syringe 100 of the health care professional, by supporting the fingers of the health care professional when using the dual chamber combined container-syringe 100.

The cylinder portion 63 has an approximately cylinder shape around the axis O, and is further extended rearward from the rear end of the fitting portion 61. An inner diameter of the cylinder portion 63 is reduced further than an inner diameter of the fitting portion 61, and the rear end of the outer casing 10 comes into contact with the step portion in the boundary between the cylinder portion 63 and the fitting portion 61. Moreover, an inner peripheral surface of the cylinder portion 63 is formed with a female screw portion 64 twisted around the axis O. The female screw portion 64 is constituted by two sets of female screws that are twisted in a clockwise direction (hereinafter, referred to as a screw rotation direction) as they go from the rear end side to the tip side of the finger grip 60, and each female screw is extended so as to be rounded over, for example, 360° of the inner peripheral surface of the cylinder portion 63.

Furthermore, the inner peripheral surface of the cylinder portion 63, that is, the female screw portion 64 is formed with a guide groove 65 that is recessed outward in the radial direction of the female screw portion 64 (the radially outward direction of the axis O) and is extended parallel to the axis O. The guide groove 65 is extended over the entire region of the cylinder portion 63 and the female screw portion 64 in the axial O direction. A pair of guide grooves 65 is provided at intervals of 180° in the circumferential direction of the female screw portion 64, that is, so as to face each other in the radial direction of the female screw portion 64.

Furthermore, the rear end of the cylinder portion 63 is provided with pairs of first protrusions 66 and second protrusions 67, respectively. The pair of first protrusions 66 is provided at intervals of 180° in the circumferential direction of the cylinder portion, that is, so as to face each other in the radial direction of the cylinder portion. Furthermore, the pair of second protrusions 67 is also provided at intervals of 180° in the circumferential direction of the cylinder portion, that is, so as to face each other in the radial direction of the cylinder portion.

The first protrusions 66 and the second protrusions 67 are formed so as to be protruded from the rear end surface 63a of the cylinder portion 63 toward the rear side of the axis O.

More specifically, the first protrusion 66 is formed in a portion of the rear side of the screw rotation direction of the pair of guide grooves 65 on the rear end surface 63a of the cylinder portion 63, and the second protrusion 67 is formed in a portion of the front side of the screw rotation direction of the pair of guide grooves 65 on the rear end surface 63a of the cylinder portion 63. As a result, the first protrusion 66 and the second protrusion 67 are adjacent to the guide grooves 65 so as to interpose the guide groove 65 therebetween from the axis O circumferential direction.

Herein, a surface facing the rear side of the screw rotation direction of the first protrusion 66 is a gentle slope surface 66a that gradually slopes from the rear end surface 63a toward the rear side of the axis O as it goes toward the front side of the screw rotation direction, and a surface facing the front side of the screw rotation direction of the first protrusion 66 is a steep slope surface 66b that gradually slopes toward the front side of the axis O as it goes toward the front side of the screw rotation direction.

The steep slope surface 66b has the steeper slope than the gentle slope surface 66a.

In addition, a surface facing the rear side of the screw rotation direction in the second protrusion 67 is a vertical surface 67a that is vertically extended from the rear end surface 63a of the cylinder portion 63 connected to the guide groove 65 to the rear side of the axis O.

In addition, the second protrusion 67 is formed to be higher than the first protrusion 66, that is, an apex portion of the vertical surface 67a of the second protrusion 67 is situated in the rear side of the axial O direction further than an apex portion of the first protrusion 66.

Figure 3:
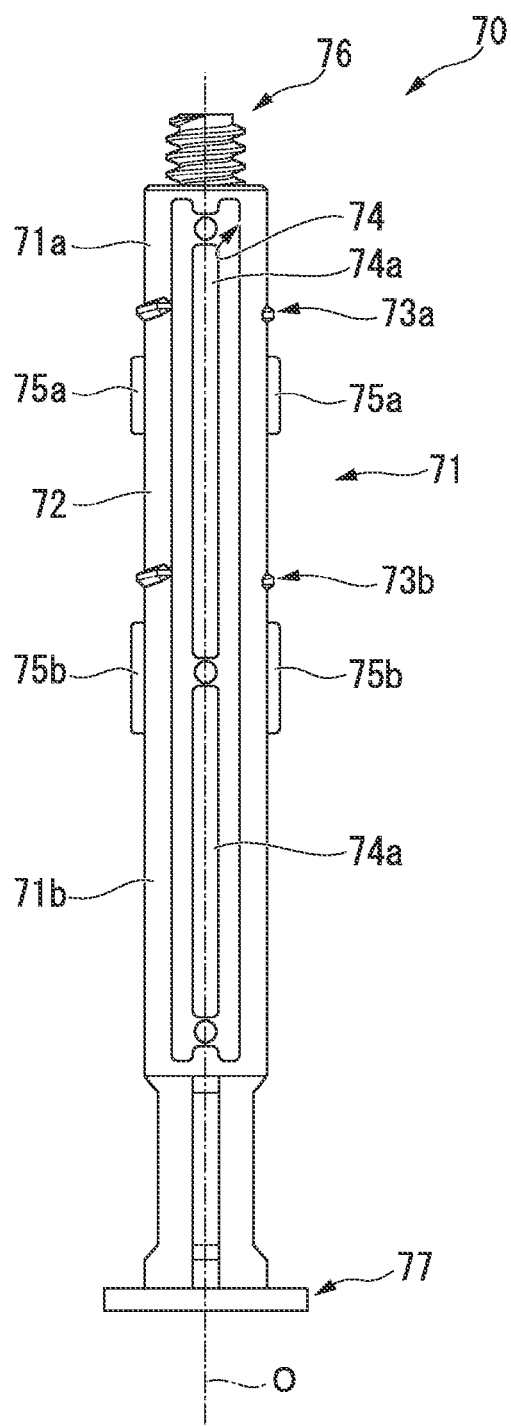
FIG. 3 is a side view of a plunger rod.
Figure 4:
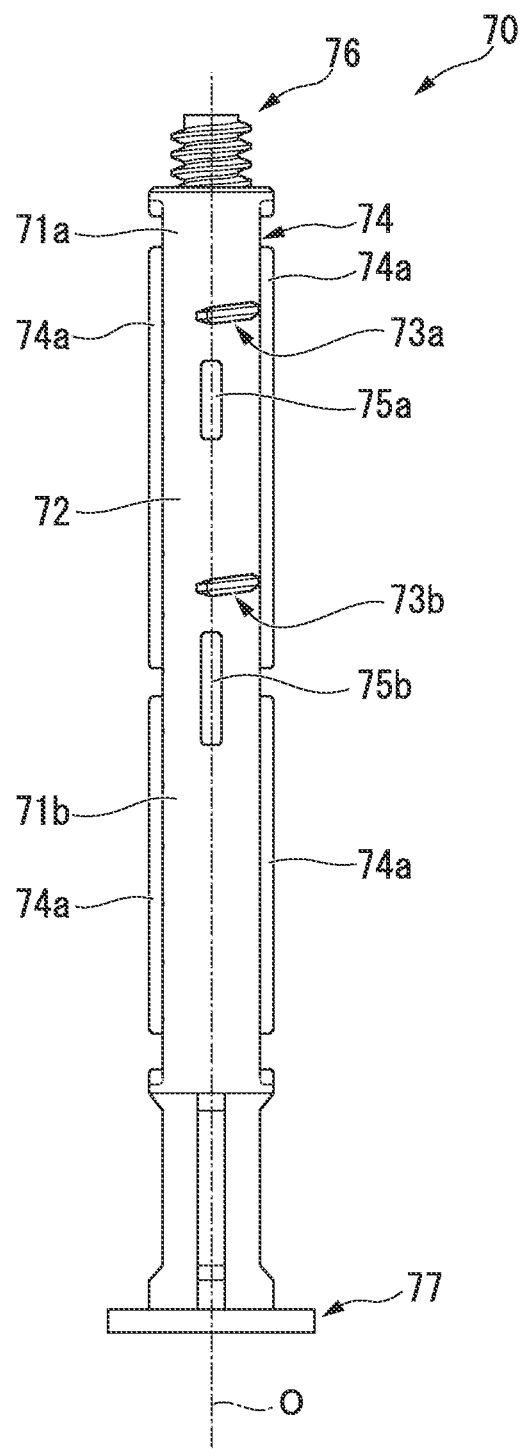
FIG. 4 is a side view of the plunger rod.
Figure 5:
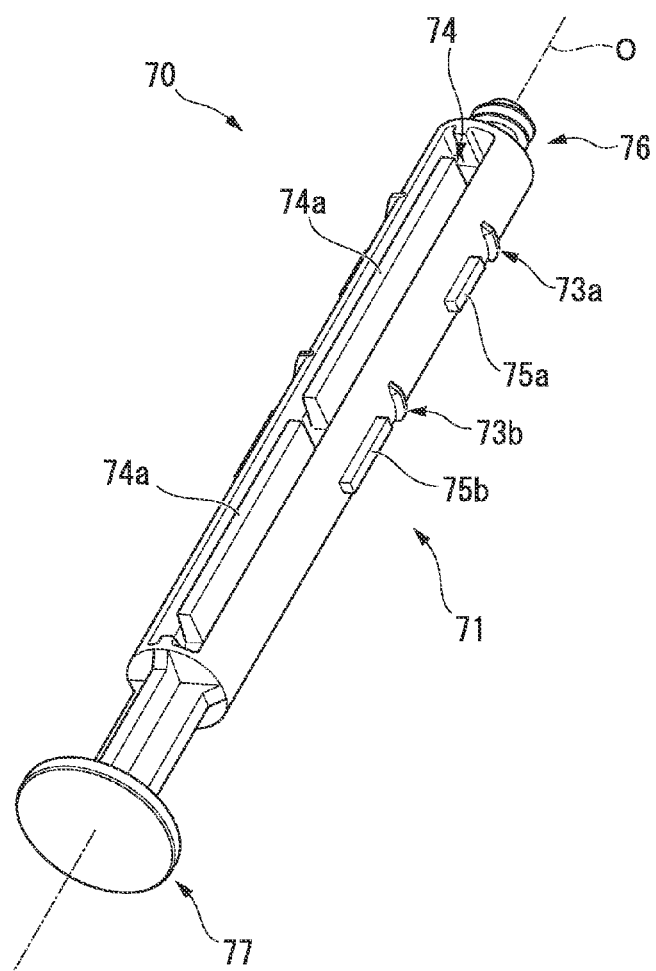
FIG. 5 is a perspective view of the plunger rod.

The plunger rod 70 is a member that is connected to the end stopper 50 so as to move the end stopper 50 toward the front side of the outer casing 10. As shown in FIGS. 3 to 5, the plunger rod 70 includes a rod portion 71 that forms an elongated shape extending along the axis O, a connection portion 76 that is provided at the tip side of the rod portion 71 and forms a male screw shape to be connected to the end stopper 50, and a pushing portion 77 that is provided in the rear end side of the rod portion 71 and is pressed by a health care professional when pushing the end stopper 50.

Furthermore, the outer peripheral surface of the rod portion 71 is provided with first male screw portions 73a twisted around the axis O, and second male screw portions 73b are formed on the rear end side of the first male screw portion 73a at intervals. The first male screw portions 73a and the second male screw portions 73b are constituted by two sets of male screws that are twisted in the clockwise direction (the screw rotation direction) as they go from the rear end side toward the front end side of the plunger rod 70, respectively.

The two sets of male screws of each of the first male screw portion 73a and the second male screw portion 73b are formed symmetrically with the axis O interposed therebetween, and, for example, are extended over approximately ⅙ of the outer periphery size of the rod portion 71.

In addition, the rod portion 71 is provided with a pair of notch portions 74 that is formed so as to notch a predetermined range of the circumferential direction over almost the whole regions of the axial O direction. The pair of notch portions 74 is formed at intervals of 180° in the circumferential direction of the rod portion 71. As a result, the molding of the rod portion 71 by a split mold is possible.

Furthermore, the notch portions 74 are formed with ribs 74a that are protruded from the bottom surface of the notch portion 74, that is, the surface facing the outside of the radial direction of the axis O in the notch portions 74 to the outside of the radial direction of the axis O and are extended parallel to the axis O. The strength of the rod portion 71 is held by the rib portion 74a. Furthermore, two ribs 74a are juxtaposed in each notch portion 74 in the axial O direction. In this manner, by a configuration in which the rib 74a of the tip side and the rib 74a of the rear end side are divided from each other, a situation is avoided in which a part of the liquid medicine L remaining in the bulging portion of the bypass portion 11 follows the rib 74a of the tip side, and reaches the rib 74a of the rear end side, thereby becoming attached to the hand of a health care professional.

Furthermore, a region of the tip side of the region formed with the first male screw portion 73a in the rod portion 71 is a rod tip portion 71a having an outer peripheral surface of a cylinder surface shape, and a region of the rear end side of the region formed with the second male screw portion 73b in the rod portion 71 is similarly a rod rear end portion 71b having an outer peripheral surface of a cylinder surface shape. In addition, a region between the region formed with the first male screw portion 73a and the region formed with the second male screw portion 73b in the rod portion 71 is an insertion portion 72 having an outer peripheral surface of a cylinder shape.

The outer diameters of the rod tip portion 71a, the rod rear end portion 71b, and the insertion portion 72 are approximately equal to or slightly smaller than the inner diameter of the female screw portion 64 in the cylinder portion 63 of the finger grip 60. As a result, the rod tip portion 71a, the rod rear end portion 71b, and the insertion portion 72 can be inserted into the female screw portion 64 in the axial O direction.

In addition, the outer peripheral surface of the insertion portion 72 is formed with a pair of first guide plates 75a at intervals of 180° in the circumferential direction of the rod portion 71, and the outer peripheral surface of the rod rear end portion 71b is formed with a pair of second guide plates 75b at intervals of 180° in the circumferential direction of the rod portion 71. The first guide plate 75a and the second guide plate 75b have shapes protruded in a rectangular shape to the outside of the radial direction of the rod portion 71 on crosssectional surfaces perpendicular to the axis O and are extended parallel to the axis O over a predetermined range.

Next, a usage method of the dual chamber combined container-syringe 100 having such a configuration will be described with reference to FIGS. 6A to 6D, and 7A to 7C.

Firstly, as shown in FIG. 6A, by screwing the connection portion 76 at the tip of the plunger rod 70 into the female screw hole of the end stopper 50, the plunger rod 70 is connected to the end stopper 50. In this state, the rod tip portion 71a of the rod portion 71 is inserted into the female screw portion 64 of the finger grip 60.

Next, a health care professional presses the pushing portion 77 of the plunger rod 70 from the rear end side in the state of putting a finger on the flange portion 62 of the finger grip 60. The pressing force is transmitted to the middle stopper 40 via the end stopper 50 and the liquid medicine L, that is, the middle stopper 40 is also moved forward in the rear end side cylinder portion 13 of the outer casing 10 together with the forward movement of the plunger rod 70 due to the pressing force.

Moreover, as shown in FIG. 6B, when a part (in the present embodiment, a half of the tip side of the axial O direction of the middle stopper 40) of the middle stopper 40 enters the bypass portion 11, the tip of the first male screw portion 73a of the plunger rod 70 comes into contact with the rear end of the female screw portion 64 of the finger grip 60. In this manner, the first male screw portion 73a comes into contact with the female screw portion 64, whereby the first male screw portion 73a and the female screw portion 64 are a stopper of the forward movement of the plunger rod 70. Thus, even when the plunger rod 70 is pushed after that, the plunger rod 70 cannot be moved forward.

Furthermore, in this manner, the first male screw portion 73a comes into contact with the female screw portion 64, whereby the first male screw portion 73a can be screwed into the female screw portion 64. Thus, upon rotating the plunger rod 70 to the front side of the screw rotation direction in this state, the plunger rod 70 is screwed into the first male screw portion 73a and the female screw portion 64 and is slightly moved forward according to the pitches of the first male screw portion 73a and the female screw portion 64.

Moreover, as shown in FIG. 6C, in the state in which the first male screw portion 73a is screwed into the female screw portion 64, the first guide plate 75a of the plunger rod 70 comes into contact with the gentle slope surface 66a of the first protrusion 66 of the finger grip 60 so that the former can climb over the latter from the rear side of the screw rotation direction.

Herein, the state, in which the first guide plate 75a comes into contact with the first protrusion 66 in a climbable manner, refers to a contact state in which the resistance of the rotation of the plunger rod 70 is generated by the contact of the first guide plate 75a to the gentle slope surface 66a of the first protrusion 66, but the first guide plate 75a can be made to climb over the first protrusion 66 in the front side of the screw rotation direction by strongly rotating the plunger rod 70. Such a contact state can be realized by molding the plunger rod 70 and the finger grip 60 by a material having flexibility such as synthetic resin.

Moreover, when the first guide plate 75a is made to climb over the first protrusion 66 by strongly rotating the plunger rod 70 in the contact state, next, the first guide plate 75a comes into contact with the vertical surface 67a of the second protrusion 67 from the rear side of the screw rotation direction. As a result, the movement of the guide plate 75 to the front side of the screw rotation direction is inhibited, that is, it is not possible to further rotate the plunger rod 70 to the front side of the screw rotation direction. In addition, even if the plunger rod 70 is rotated in the opposite direction of the screw rotation direction, the first guide plate 75a comes into contact with the steep slope surface 66b of the first protrusion 66, whereby the rotation is inhibited.

In addition, after the first guide plate 75a climbs over the first protrusion 66 as above, the first male screw portion 73a passes through the region in which the female screw portion 64 exists, that is, the first male screw portion 73a and the female screw portion 64 are unscrewed. At this time, since the insertion portion 72 is inserted into the female screw portion 64, the pushing of the plunger rod 70 is possible again.

Furthermore, when the first guide plate 75a is situated between the first protrusion 66 and the second protrusion 67, the circumferential direction positions of the first guide plate 75a and guide groove 65 of the finger grip 60 coincide with each other, that is, the first guide plate 75a can be fitted into the guide groove 65, and the plunger rod 70 enters a straightly-movable state.

After that, upon pushing of the plunger rod 70, the guide plate 75 of the plunger rod 70 is fitted into the guide groove 65 of the finger grip 60, and the plunger rod 70 is moved forward so as to be guided by the guide groove 65. In addition, the pushing of the plunger rod 70 by a health care professional is carefully performed so that the forward movement speed of the plunger rod 70 can be suppressed. Moreover, as shown in FIG. 6D, the entire length of the middle stopper 40 in the axial O direction enters the bypass portion 11, the front chamber F and the rear chamber B communicate with each other via the bulging region to the outside of the outer casing 10 in the bypass portion 11.

As a result, the liquid medicine L of the rear chamber B can flow in the pharmaceutical preparation S of the front chamber F. Moreover, when a health care professional carefully further pushes the plunger rod 70, the most of the pressing force to be applied to the liquid medicine L by the forward movement of the plunger rod 70 is converted to the pressure for causing the liquid medicine L to flow in the front chamber F. Thus, the middle stopper 40 hardly moves forward at all and can remain in the bypass portion 11.

After that, when the tip of the end stopper 50 comes into contact with the rear end of the middle stopper 40 due to the forward movement of the plunger rod 70, the entire liquid medicine L in the rear chamber B is introduced into the pharmaceutical preparation S in the front chamber F, whereby the rear chamber B is dissipated. Moreover, upon further pushing the plunger rod 70 to gradually move the plunger rod 70 forward, the middle stopper 40 coming into contact with the end stopper 50 is also simultaneously moved forward via the end stopper 50.

Figure 7B:
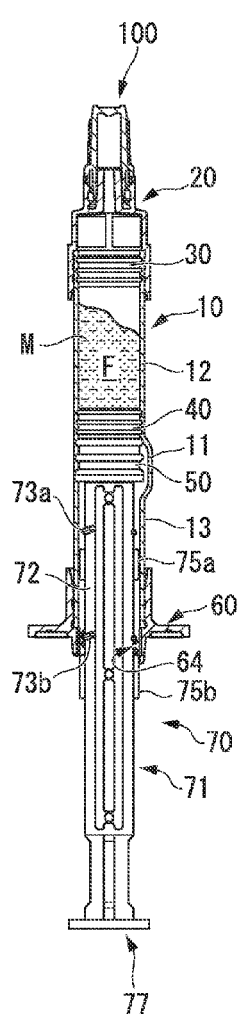
FIG. 7B is a diagram that shows a usage method of the dual chamber combined container-syringe according to an embodiment.

Next, as shown in FIG. 7B, when the middle stopper 40 enters the tip side cylinder portion 12 of the outer casing 10, that is, when the middle stopper 40 deviates from the bypass portion 11, the tip of the second male screw portion 73b of the plunger rod 70 comes into contact with the female screw portion 64 of the finger grip 60. In this manner, the second male screw portion 73b comes into contact with the female screw portion 64, whereby the second male screw portion 73b and the female screw portion 64 are a stopper of the forward movement of the plunger rod 70. Thus, after that, even when the plunger rod 70 is pushed, the plunger 70 is not moved forward.

Furthermore, in this manner, the second male screw portion 73b comes into contact with the female screw portion 64, whereby the second male screw portion 73b can be screwed into the female screw portion 64. Thus, upon rotating the plunger rod 70 in the front side of the screw rotation direction in this state, the plunger rod 70 is screwed into the second male screw portion 73b and the female screw portion 64 and is slightly moved forward according to the pitches of the second male screw portion 73b and the female screw portion 64.

Moreover, when the second male screw portion 73b is screwed into the female screw portion 64 by the rotation to the front side of the screw rotation direction of the plunger rod 70, the second guide plate 75b of the plunger rod 70 can come into contact with the gentle slope surface 66a of the first protrusion 66 of the finger grip 60 so that the former can move over the latter from the rear side of the screw rotation direction. At this time, the front chamber F enters the sealed state again, and a health care professional shakes the dual chamber combined container-syringe 100 at this time, whereby the pharmaceutical preparation S is completely dissolved in the liquid medicine L and the injection drug M can be prepared.

In addition, the state, in which the second guide plate 75b comes into contact with the first protrusion 66 in a movable manner, refers to a state in which the first guide plate 75a can come into contact with the first protrusion 66 in a movable manner.

Moreover, when the second guide plate 75b moves over the first protrusion 66 by strongly rotating the plunger rod 70 in the contact state, next, the second guide plate 75b comes into contact with the vertical surface 67a of the second protrusion 67 from the rear side of the screw rotation direction. As a result, the movement of the second guide plate 75b to the front side of the screw rotation direction is inhibited, that is, it is not possible to further rotate the plunger rod 70 to the front side of the screw rotation direction. In addition, even if the plunger rod 70 is rotated in the opposite direction of the screw rotation direction, the second guide plate 75b comes into contact with the steep slope surface 66b of the first protrusion 66, whereby the rotation is inhibited.

In addition, after the second guide plate 75b climbs over the first protrusion 66 as above, the second male screw portion 73b passes through the region in which the female screw portion 64 exists, that is, the second male screw portion 73b and the female screw portion 64 are unscrewed. As a result, the forward movement due to the straight movement of the plunger rod 70 is possible again.

Furthermore, when the second guide plate 75b is situated between the first protrusion 66 and the second protrusion 67, the circumferential direction positions of the second guide plate 75b and the guide groove 65 of the finger grip 60 coincide with each other, that is, the second guide plate 75b can be fitted into the guide groove 65.

After that, upon pushing of the plunger rod 70, the second guide plate 75b of the plunger rod 70 is fitted into the guide groove 65 of the finger grip 60, and the plunger rod 70 is moved forward so as to be guided by the guide groove 65. In addition, the pressing force generated by pushing the plunger rod 70 at this time is transmitted to the front stopper 30 via the end stopper 50, the middle stopper 40, and the injection drug M, and the front stopper 30 is moved forward in the outer casing 10.

Moreover, when the front stopper 30 goes into the bypass chamber 25 as a result of the forward movement of the front stopper 30, the front chamber F where the injection drug M exists communicates with the injection hole 23a of the lure point 23 via the bypass groove 26. As a result, the air bubbles remaining in the outer casing 10 are discharged to the outside, and the injection drug M can be introduced to the injection needle 27, whereby the injection drug M can be administered to a patient.

Figure 7C:
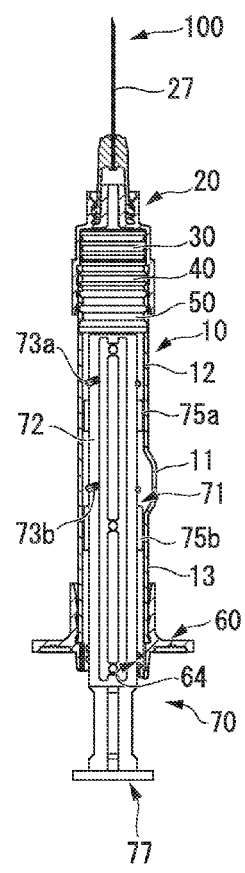
FIG. 7C is a diagram that shows a usage method of the dual chamber combined container-syringe according to an embodiment.

After that, when performing the administration of the injection drug M, by further pushing the plunger rod 70, the injection drug M of the front chamber F is introduced to the injection needle 27 via the bypass groove 26 and the injection hole 23a. Moreover, when the plunger rod 70 is completely pushed, as shown in FIG. 7C, the whole injection drug M is discharged to the outside via the injection needle 27, the tip of the middle stopper 40 comes into contact with the rear end of the front stopper 30, and the front chamber F is dissipated. From the above, the administration of the injection drug M to a patient is finished.

In this manner, according to the dual chamber combined container-syringe 100 of the present embodiment, when the middle stopper 40 is moved forward via the end stopper 50 and the liquid medicine L by pushing the plunger rod 70, the tip of the first male screw portion 73a comes into contact with the rear end of the female screw portion 64 when a part of the middle stopper 40 enters the bypass portion 11. Moreover, after that, if the plunger rod 70 is not rotated according to the first male screw portion 73a and the female screw portion 64 being screwed, the plunger rod 70 is not moved forward.

Thus, even if the plunger rod 70 is erroneously further pushed, the plunger rod 70 is not moved forward, and thus, the middle stopper 40 is not moved forward. Thus, if the plunger rod 70 is erroneously too pushed, it is possible to avoid a case where the middle stopper 40 is moved too forward to the tip side of the bypass portion 11. Thus, since the entering of the middle stopper 40 to the bypass portion 11 at the correct timing is promoted and it is possible to ensure the state in which the front chamber F communicates with the rear chamber B, it is possible to suitably mix the liquid medicine L with the pharmaceutical preparation S.

Furthermore, after the first male screw portion 73a passes through the female screw portion 64, the insertion portion 72 of the plunger rod 70 can be inserted into the female screw portion 64, whereby the plunger rod is moved forward by pushing the plunger rod 70. Moreover, the pressing force applied along with the forward movement of the plunger rod 70 works only so as to cause the liquid medicine L to flow into the front chamber F, and at that time, the middle stopper 40 remains in the bypass portion 11 almost without being moved forward. When all the liquid medicine L in the rear chamber B flows in the front chamber F, the tip of the end stopper 50 comes into contact with the rear end of the middle stopper 40. After that, when the middle stopper 40 is moved forward together with the end stopper 50, before the rear portion of the end stopper 50 passes through the bypass portion 11, the tip of the second male screw portion 64 comes into contact with the rear end of the female screw portion 64. Particularly, in the present embodiment, when a part of the middle stopper 40 passes through the bypass portion 11, the tip of the second male screw portion 73b comes into contact with the rear end of the female screw portion 64. As a result, a health care professional can easily recognize that the front chamber F is sealed again, whereby it is possible to prepare the injection drug M in which the pharmaceutical preparation S is completely dissolved in the liquid medicine L by shaking the dual chamber combined container-syringe 100 in this state.

After that, after the second male screw portion 73b of the plunger rod 70 passes through the female screw portion 64 by rotating the plunger rod 70, the plunger rod 70 enters the pushable state. At this state, by fitting the second guide plate 75b of the plunger rod 70 to the guide groove 65 formed in the female screw portion 64, the plunger rod 70 can be moved straight forward.

In addition, by rotating the plunger rod 70 after the first male screw portion 73a or the second male screw portion 73b comes into contact with the female screw portion 64, it is possible to obtain a sensation when the first guide plate 75a or the second guide plate 75b comes into contact with the first protrusion 66. As a result, it is possible to cause a health care professional to easily and reliably recognize the timing of the important works such as the in-flow of the liquid medicine L of the rear chamber B to the front chamber F, the mixture of the liquid medicine L and the pharmaceutical preparation S flown in the front chamber F, and the dissolution thereof that are performed later.

Furthermore, in the present embodiment, by bringing the first guide plate 75a or the second guide plate 75b into contact with the second protrusion 67 by rotating the plunger rod 70, the first guide plate 75a or the second guide plate 75b can be fitted into the guide groove 65 of the finger grip 60. Thus, after that, the plunger rod 70 can enter the forward-movable state, whereby the contents of the work can reliably be changed by the operation switch-over between the rotation and the straight movement.

As mentioned above, the dual chamber combined container-syringe 100 as an embodiment of the present embodiment was described in detail, but the present invention is not limited thereto without departing from the technical scope of the present invention, and a slight design change or the like is possible.

In addition, even if the plunger rod 70 is carelessly pushed when packaging the dual chamber combined container-syringe 100 in the state in which the plunger rod 70 is connected to the end stopper 50, the first male screw portion 73a comes into contact with the female screw portion 64, whereby the further forward movement of the plunger rod 70 is impeded. Thus, the separation state between the liquid medicine L and the pharmaceutical preparation S can always reliably be maintained, and the risk can be avoided.

Figure 9A:
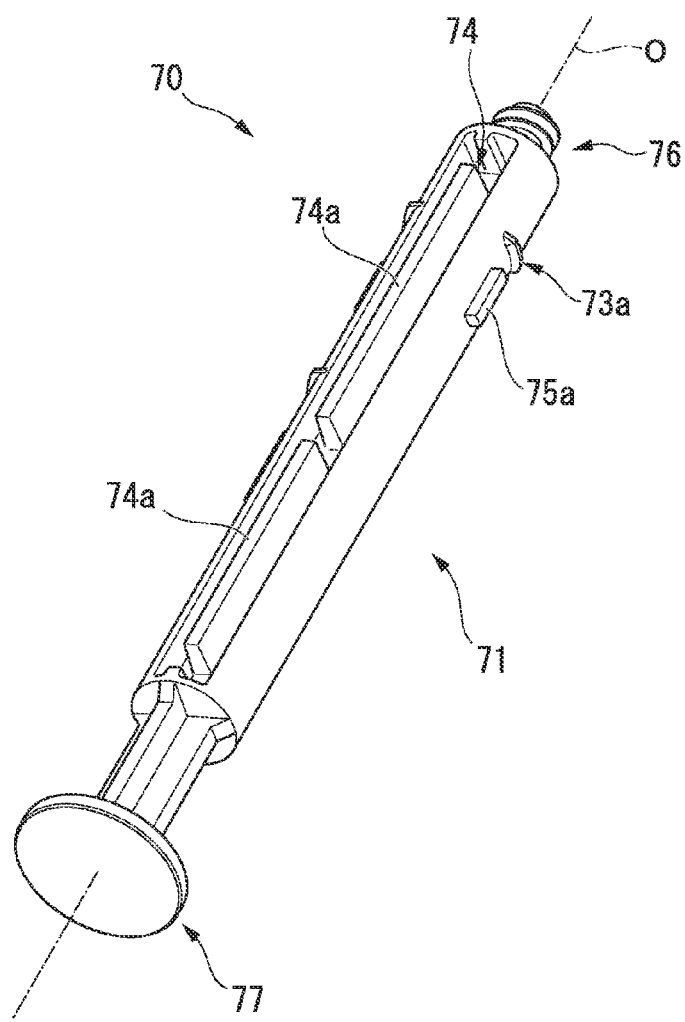
FIG. 9A is a perspective view of the plunger rod according to an alternative embodiment.

Furthermore, in the present embodiment, the plunger rod 70 formed with both of the first male screw portion 73a and the second male screw portion 73b was described, but the present invention is not limited thereto. As shown in FIG. 9A, only the first male screw portion 73a may be formed or only the second male screw portion 73b may be formed as shown in FIG. 9B.

At this time, when only the first male screw portion 73a is formed as shown in FIG. 9A, only the first guide plate 75a may be formed accordingly, and there is no need to form the second guide plate 75b. Further, when only the second male screw portion 73b is formed as shown in FIG. 9B, only the second guide plate 75b may be formed accordingly, and there is no need to form the first guide plate 75a.

Figure 9B:
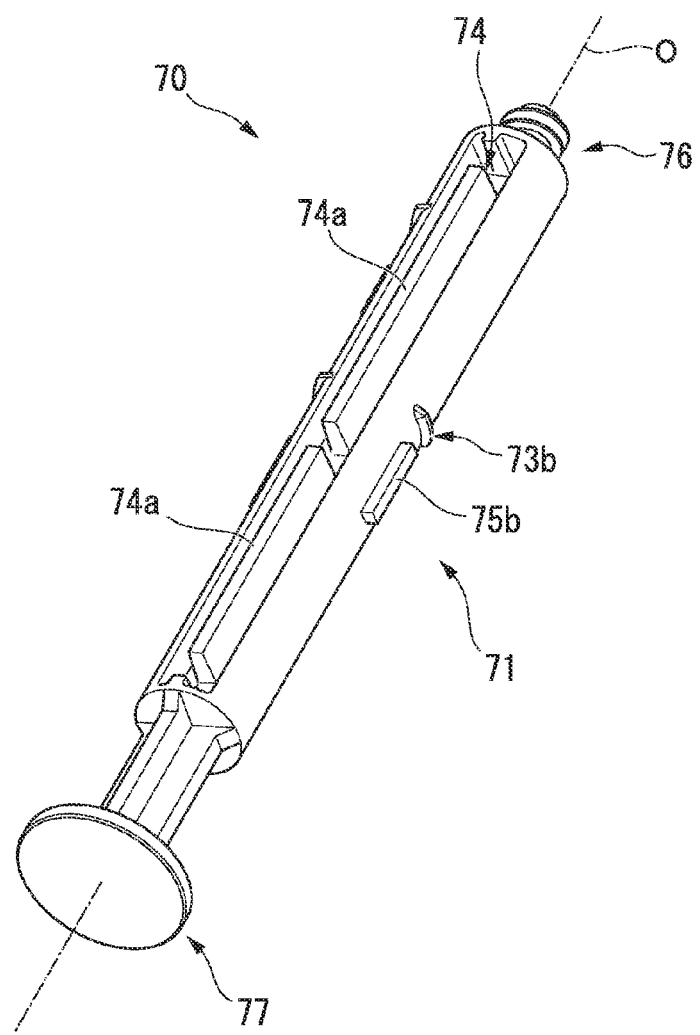
FIG. 9B is a perspective view of the plunger rod according to an alternative embodiment.

Furthermore, in the configurations shown in FIGS. 9A and 9B, a configuration may be adopted in which the first guide plate 75a and the second guide plate 75b are not formed.

Figure 2A:
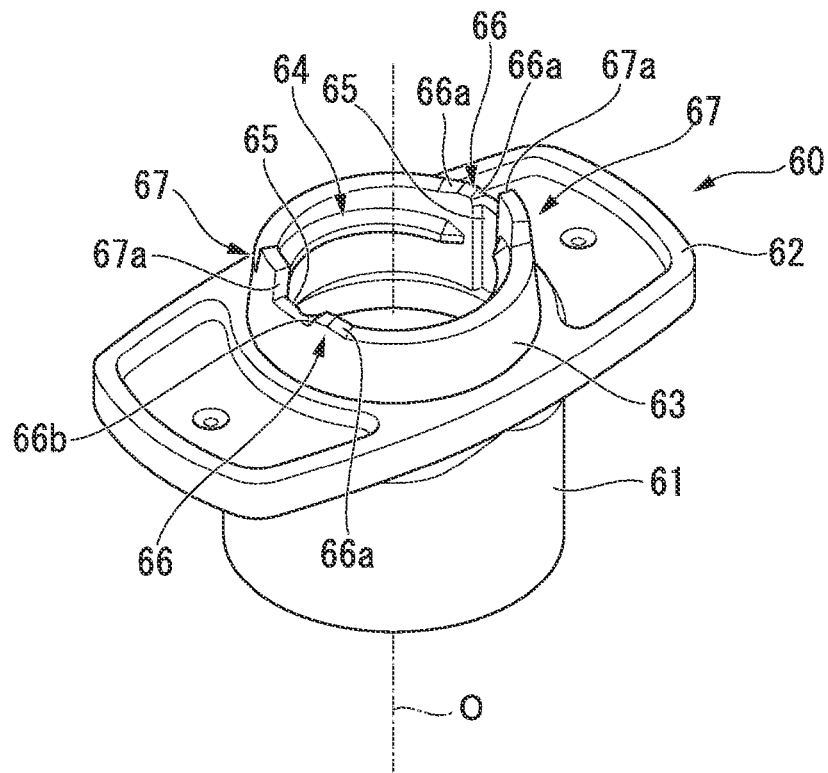
FIG. 2A is a perspective view that shows a finger grip.
Figure 2B:
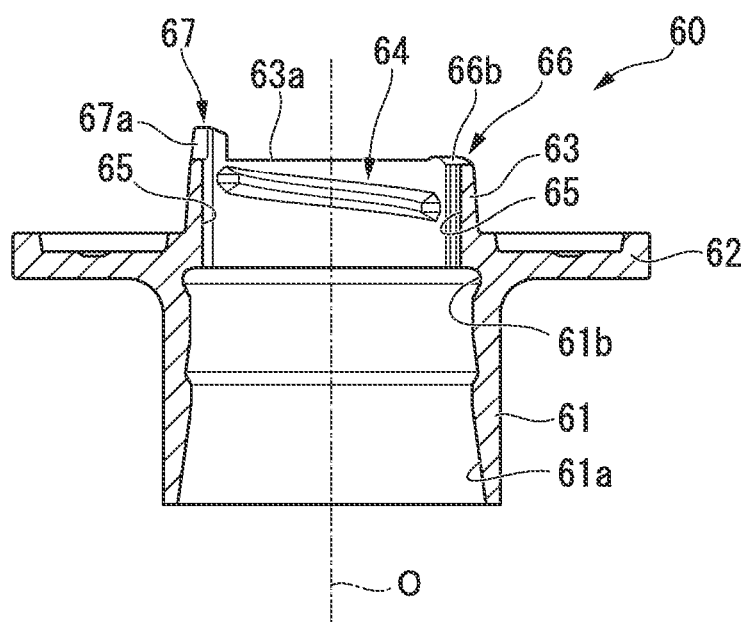
FIG. 2B is a longitudinal cross-sectional view that shows the finger grip.
Figure 8A:
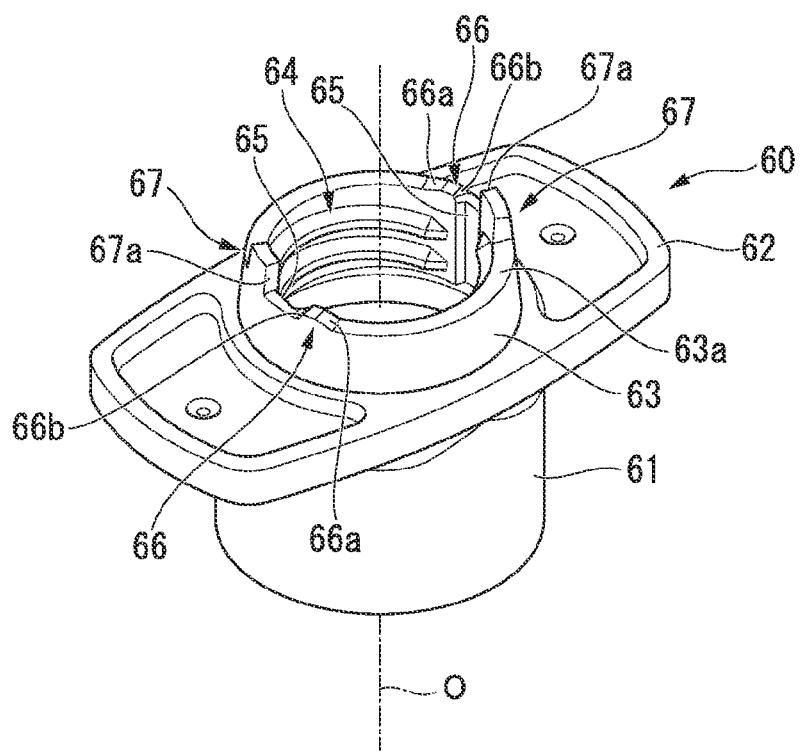
FIG. 8A is a perspective view that shows the finger grip.
Figure 8B:
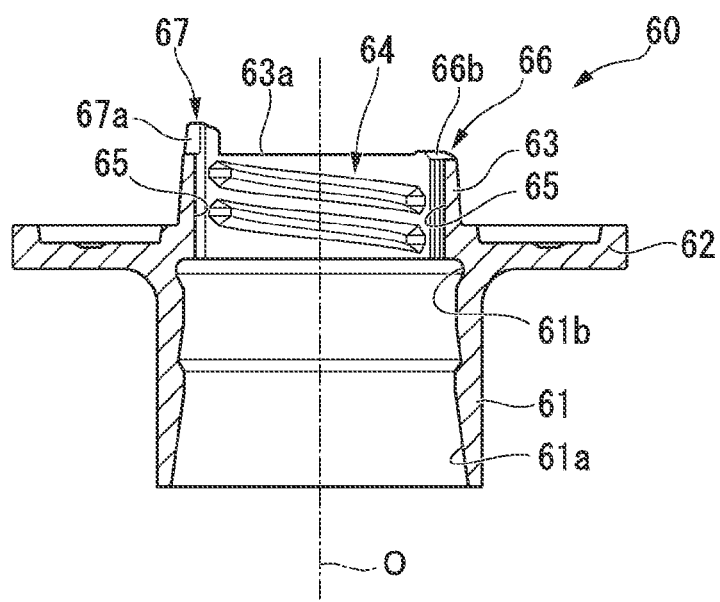
FIG. 8B is a longitudinal cross-sectional view that shows the finger grip.

In addition, in the finger grip 60 of the present embodiment, as shown in FIGS. 2A and 2B, two sets of female screw forming the male screw portion 64 are formed over a half circumference (180°). However, as shown in FIGS. 8A and 8B, two sets of female screw forming the female screw portion 64 may overlap with the axis O, that is, may be formed over one circumference (360°).

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A dual chamber combined container-syringe comprising:
   an outer casing which forms a cylinder shape around an axis, and has a bypass portion formed by an outward bulging of a part of an inner peripheral surface;
   a hub lure lock provided in a tip of the outer casing;

a finger grip provided in a rear end of the outer casing;

a front stopper that is fitted to a tip side of the bypass portion in the outer casing;

a middle stopper that is fitted to a rear end side of the bypass portion in the outer casing and seals a pharmaceutical preparation into a first section of the outer casing together with the front stopper;

an end stopper that is fitted to a rear end side of the middle stopper in the outer casing and seals a liquid medicine into a second section of the outer casing together with the middle stopper; and a plunger rod that is inserted into the finger grip and is connected to the end stopper from a rear end side of the end stopper, wherein an inner peripheral surface of the finger grip is formed with a female screw portion that is twisted around the axis, and an outer peripheral surface of the plunger rod is formed with a first male screw portion that is capable of being screwed into the female screw portion, when a part of the middle stopper, which is moved forward, enters the bypass portion by pushing the plunger rod, a tip of the first male screw portion comes into contact with a rear end of the female screw portion, after the tip of the first male screw portion comes into contact with the rear end of the female screw portion, the first male screw portion is screwed into the female screw portion by moving the middle stopper forward while rotating the plunger rod with respect to the finger grip;

before the middle stopper completely enters the bypass portion by further moving the middle stopper forward by rotating the plunger rod with respect to the finger grip, the screwing of the first male screw portion into the female screw portion is released;

a guide groove is formed in the female screw portion of the finger grip, the guide groove being extended parallel to the axis;

a first guide plate is formed on the outer peripheral surface of the plunger rod at a position further to a rear end side of the plunger rod than the first male screw portion, the first guide plate being guided along the guide groove;

a first protrusion is formed in a rear end of the finger grip, the first protrusion coming into contact with the first guide plate so that the first guide plate climbs over the first protrusion when the first male screw portion is screwed into the female screw portion;

after the first guide plate moves over the first protrusion, the screwing of the first male screw portion into the female screw portion is released; and a second protrusion is formed in the rear end of the finger grip, the second protrusion coming into contact with the first guide plate which has climbed over the first protrusion in a position where the first guide plate is fitted into the guide groove.

2. The dual chamber combined container-syringe according to claim 1, wherein a second male screw portion capable of being screwed into the female screw portion is formed on the outer peripheral surface of the plunger rod at a position further to the rear end side of the plunger rod than the first male screw portion, after a part of the middle stopper, which is moved forward, passes through the bypass portion by pushing the plunger rod, a tip of the second male screw portion comes into contact with the rear end of the female screw portion, after the tip of the second male screw portion comes into contact with the rear end of the female screw portion, the second male screw portion is screwed into the female screw portion by moving the middle stopper forward while rotating the plunger rod with respect to the finger grip; and before a rear portion of the end stopper passes through the bypass portion by further moving the middle stopper forward while rotating the plunger rod with respect to the finger grip, the screwing of the second male screw portion into the female screw portion is released.

3. The dual chamber combined container-syringe according to claim 2, further comprising:

a second guide plate that is formed at the rear end side of the second male screw portion on the outer peripheral surface of the plunger rod and is guided along the guide groove.

4. The dual chamber combined container-syringe according to claim 3, wherein the first protrusion comes into contact with the second guide plate so that the second guide plate can climb thereover when the second male screw portion is screwed into the female screw portion, and after the second guide plate climbs over the first protrusion, the female screw portion and the second male screw portion are unscrewed.

5. The dual chamber combined container-syringe according to claim 4, wherein the second protrusion comes into contact with the second guide plate in a position where the second guide plate climbing over the first protrusion is fitted into the guide groove.

6. A dual chamber combined container-syringe comprising:

an outer casing which forms a cylinder shape around an axis, and has a bypass portion formed by an outward bulging of a part of an inner peripheral surface;

a hub lure lock provided in a tip of the outer casing;

a finger grip provided in a rear end of the outer casing;

a front stopper that is fitted to a tip side of the bypass portion in the outer casing;

a middle stopper that is fitted to a rear end side of the bypass portion in the outer casing and seals a pharmaceutical preparation into a first section of the outer casing together with the front stopper;

an end stopper that is fitted to a rear end side of the middle stopper in the outer casing and seals a liquid medicine into a second section of the outer casing together with the middle stopper; and a plunger rod that is inserted into the finger grip and is connected to the end stopper from a rear end side of the end stopper, wherein an inner peripheral surface of the finger grip is formed with a female screw portion twisted around the axis, and an outer peripheral surface of the plunger rod is formed with a second male screw portion that is capable of being screwed into the female screw portion, after a part of the middle stopper, which is moved forward, passes through the bypass portion by pushing the plunger rod, a tip of the second male screw portion comes into contact with a rear end of the female screw portion, after the tip of the second male screw portion comes into contact with the rear end of the female screw portion, the second male screw portion is screwed into the female screw portion by moving the middle stopper forward while rotating the plunger rod with respect to the finger grip;

before a rear portion of the end stopper passes through the bypass portion by further moving the middle stopper forward while rotating the plunger rod with respect to the finger grip, the screwing of the second male screw portion into the female screw portion is released;

a guide groove is formed in the female screw portion of the finger grip, the guide groove being extended parallel to the axis;

a second guide plate is formed on the outer peripheral surface of the plunger rod at a position further to a rear end side of the plunger rod than the second male screw portion, the second guide plate being guided along the guide groove;

a first protrusion is formed in a rear end of the finger grip, the first protrusion coming into contact with the second guide plate so that the second guide plate climbs over the first protrusion when the second male screw portion is screwed into the female screw portion;

after the second guide plate moves over the first protrusion, the screwing of the second male screw portion into the female screw portion is released; and a second protrusion is formed in the rear end of the finger grip, the second protrusion coming contact with the second guide plate which has climbed over the first protrusion in a position where the second guide plate is fitted into the guide groove.

7. The dual chamber combined container-syringe according to claim 6, wherein a first male screw portion capable of being screwed into the female screw portion is formed on the outer peripheral surface of the plunger rod at a position further to a tip end side of the plunger rod than the second male screw portion, when a part of the middle stopper which is moved forward, enters the bypass portion by pushing the plunger rod, a tip of the first male screw portion comes into contact with the rear end of the female screw portion, after the tip of the first male screw portion comes into contact with the rear end of the female screw portion, the first male screw portion is screwed into the female screw portion by moving the middle stopper forward while rotating the plunger rod with respect to the finger grip; and before the middle stopper completely enters the bypass portion by further moving the middle stopper forward while rotating the plunger rod with respect to the finger grip, the screwing of the first male screw portion into the female screw portion is released.

* * * * *